US007347204B1

(12) United States Patent
Lindsey et al.

(10) Patent No.: US 7,347,204 B1
(45) Date of Patent: Mar. 25, 2008

(54) BREATHING AIR SYSTEM FOR A FACILITY

(75) Inventors: Rickey Floyd Lindsey, Missouri City, TX (US); Jerry Paul Johnson, Seabrook, TX (US)

(73) Assignee: Total Safety US, Inc., Houston, TX (US)

( * ) Notice: Subject to any disclaimer, the term of this patent is extended or adjusted under 35 U.S.C. 154(b) by 637 days.

(21) Appl. No.: 11/042,622

(22) Filed: Jan. 24, 2005

Related U.S. Application Data

(60) Provisional application No. 60/540,516, filed on Jan. 29, 2004, provisional application No. 60/540,231, filed on Jan. 29, 2004.

(51) Int. Cl.
*A61M 11/00* (2006.01)

(52) U.S. Cl. ............................ 128/202.13; 128/204.18

(58) Field of Classification Search ........... 128/204.18, 128/202.13, 200.24, 204.29, 202.27, 204.25, 128/205.24, 205.25
See application file for complete search history.

(56) References Cited

U.S. PATENT DOCUMENTS

| | | | | |
|---|---|---|---|---|
| 4,510,930 A | * | 4/1985 | Garcia | 128/202.22 |
| 4,862,931 A | * | 9/1989 | Vella | 141/1 |
| 4,870,961 A | * | 10/1989 | Barnard | 128/202.27 |

* cited by examiner

*Primary Examiner*—Steven O. Douglas
(74) *Attorney, Agent, or Firm*—Buskop Law Group, PC; Wendy Buskop

(57) ABSTRACT

The breathing air system is made of a pressurized breathing air source, a continuous loop air conduit connected to the pressurized breathing air source for maintaining the breathing air at a defined pressure, a first isolation valve located between the pressurized breathing air source and the continuous loop air conduit, a first splitter is located between the first isolation valve and the continuous loop air conduit, a second splitter is connected to the continuous loop air conduit, a first auxiliary air conduit segment is connected to the second splitter, a second isolation valve connects to the first auxiliary air conduit segment, a reserve manifold is also used and a second auxiliary air conduit segment communicates between the second isolation valve and the reserve manifold to distribute breathing air to at least one reserve manifold from at least two directions wherein the breathing air is grade "D" or better.

19 Claims, 5 Drawing Sheets

BREATHING AIR SYSTEM FOR A FACILITY

The present application claims priority to U.S. Provisional Patent Application Ser. No. 60/540,516 and U.S. Provisional Patent Application Ser. No. 60/540,231, both filed on Jan. 29, 2004 now abandoned.

FIELD

Embodiments relate to a continuous loop air breathing system usable in a chemical plant, refinery or other facility where workers need to breathe good quality air while working in a harsh environment.

BACKGROUND

Ventilation systems within a building vary according to design, use, specifications and maintenance. For most systems, the primary function includes the restriction of air movement in and between various departments with specific requirements for ventilation and filtration to dilute and remove contamination, airborne microorganisms, viruses, hazardous chemicals and radioactive substances.

Various chemicals used in work processes are known to be hazardous to personnel in and around the work environment if they are not handled or ventilated properly. Vaporous chemicals, such as acetic acid, benzene, formaldehyde, nitrous oxide and xylene, can often affect the immune system and do carry health warnings.

Situations arise wherein volatile, toxic and particulate laden gasses are generated or leak into an interior room of a building or other confined spaces. The presence of gasses, such as vapors from hydrocarbon based products, as well as natural or liquefied petroleum gasses often occur within an enclosure or confined space, such as an interior room of a building. Volatile organic compounds such as automobile and aircraft paints, resurfacing materials, porcelain paints, reducers, glues, cleaning agents, grain dust and hydrocarbon fumes must be carefully evacuated from an interior space to avoid adverse effects, including unwanted combustion of such materials. In many instances, such materials cannot be safely or conveniently vented to the atmosphere and treatment of such gaseous material may be required to occur within the interior space.

Persons in industrialized nations spend more than 90% of their time indoors and industry-related occupations having to work in prolonged harsh conditions suffer from lung complications. The lung is the most common site of injury by airborne pollutants. Acute effects may also include non-respiratory signs and symptoms, which may also depend upon toxicological characteristics of the substances and host-related factors.

Accordingly, there has been an acute need to develop a more efficient system for handling various types of pollutants, toxic gasses and vapors, particularly with regard to interior facilities to help increase air quality. It is to these ends that the present invention has been developed.

The present system is designed to provide at least “Grade D” air to workers in a facility. The grades of air quality are determined by the Compressed Gas Association of Washington D.C. National Institute of Occupational Safety and Health, and the National Fire Protection Association and also appear in OSHA regulations Code of Federal Regulations, (CFR) Section 1910.134.

BRIEF DESCRIPTION OF THE DRAWINGS

In the detailed description of the preferred embodiments of the system presented below, reference is made to the accompanying drawings, in which.

Figure 1:
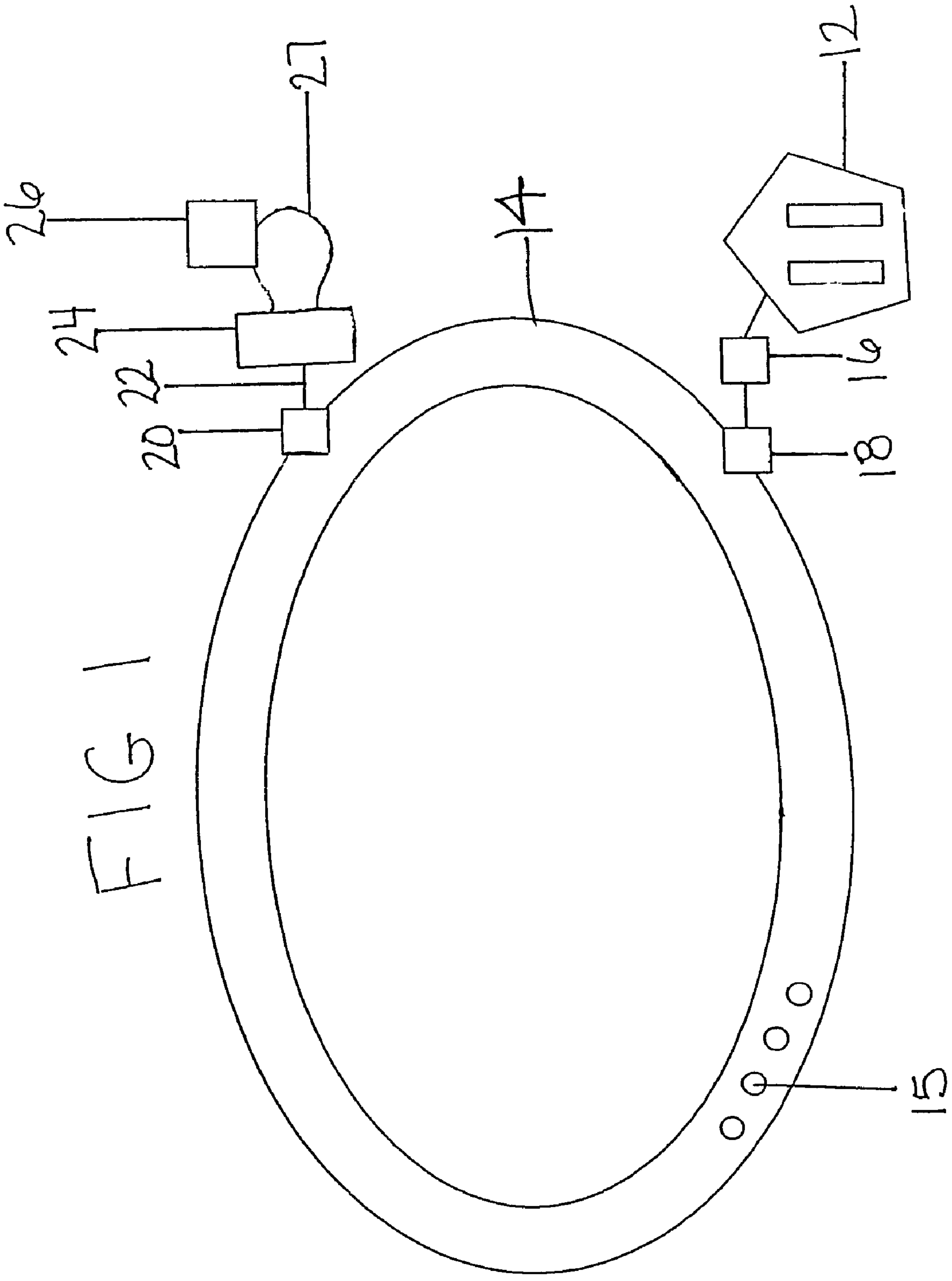
FIG. 1 is a schematic view of the system using one reserve manifold.

The present system is detailed below with reference to the listed Figures.

DETAILED DESCRIPTION OF THE PREFERRED EMBODIMENTS

Before explaining the present system in detail, it is to be understood that the system is not limited to the particular embodiments and that it can be practiced or carried out in various ways.

The breathing air system is made of a pressurized breathing air source and a continuous loop air conduit connected to the pressurized breathing air source for maintaining the breathing air at a defined pressure.

The present embodiments provide the benefits of plant safety. The system improves safety by providing clean air to workers in hazardous chemical plants and refining operations. The air is safe, contained, of the right pressure to breath, and accessible at numerous points throughout a plant without fear of failure.

The system provides the benefit of improving plant efficiency and cost savings by reducing plant traffic. The embodied system eliminates the movement of cascade breathing air systems and provides a single source of air for the workers. Traditional breathing air cascade systems that utilize cylinders of air, T-boxes, and related apparatus cause accidents like back injuries, when workers try to move the systems throughout the plant. The traditional air systems of pressurized tanks can be run over in the plant, can be dropped accidentally, and can roll unexpectedly into traffic causing damage to workers and equipment. The embodied systems provide a solution that eliminates all of these problems.

The embodied systems provide a benefit in that workers do not have to “bottle watch” to determine how much air is left in a traditional air tank. The embodied systems provide one, continuous air source to supply all the jobs or a large group of jobs in the plant. The traditional breathing air cascade systems supply only one or two workers or a small group of workers in the plant. The embodied systems significantly reduce costs and increase safety, thereby making the manufacturing plant a better more cost effective facility.

Still another benefit of the present system is that the system provides a “standard” method for providing air throughout the plant that eliminates confusion with the workers as to whether the air is on, whether the air the right pressure, and other similar variables associated with traditional breathing air cascade systems.

The system is “pre-rigged” before any work is initiated. This benefit reduces the amount of set up time needed by workers, thereby reducing labor costs at the plant.

The embodied breathing air system includes a first valve, preferably an isolation valve, like a ball valve, located between the pressurized breathing air source and an air conduit. Typically, the air conduit is a continuous loop. Examples of valves usable as the first valve can be a half-inch ball valve available from Parker Hannifin of Cleveland, Ohio.

A first splitter is located between the first valve and the air conduit, preferably a continuous loop air conduit. A second splitter is connected to the air conduit apart from the first splitter. The splitters can be T block splitters, such as those available from Air Systems International of Chesapeake, Va.

A first auxiliary air conduit segment is connected to the second splitter. The first auxiliary air conduit segment is preferably a neoprene high pressure hose available from Gates Corporation of Denver Colo. A preferred diameter for the first auxiliary air conduit segment is ⅝ inch diameter, but the diameter can range up to 1½ inch diameter hose. Although neoprene is a preferred material, stainless steel tubing or braided hose can be used. These alternative types of conduit can be acquired from Gates Corporation as well.

A second isolation valve connects to the first auxiliary air conduit segment. A second auxiliary air conduit segment communicates between the second isolation valve and at least one manifold. The breathing air system is adapted to distribute breathing air to one or more manifolds from at least two directions. The manifold is adapted to provide at least grade "D" breathing air, as identified by the Compressed Gas Association of the United States. An example of the manifolds useable with the system are Killer Bee™ manifolds manufactured by Total Safety in Houston, Tex. The preferred manifold is an eight-way manifold with a pressure regulator and a low pressure warning alarm preferably mounted on a stand.

With reference to the figures, FIG. 1 depicts a schematic view of the breathing air system using one reserve manifold. The embodied systems are typically used as a breathing air system for a facility, such as a chemical plant. The system includes a pressurized breathing air source (12), a continuous loop air conduit (14) connected to the pressurized air source (12) for maintaining pressurized breathing air (15) and a first isolation valve (16) disposed between the pressurized air source (12) and a first splitter (18). The continuous loop air conduit can be a hose, tubing, pipe or combinations thereof.

The pressurized breathing air (15) is preferably pressurized to between 500 psi and 5000 psi, and more preferably to between 2400 psi and 5000 psi.

A second splitter (20) is connected to the continuous loop air conduit (14). A first auxiliary air conduit segment (22) is connected to the second splitter (20). A second isolation valve (24) is connected to the first auxiliary air conduit segment (22). The splitter is preferably a T-block with an inner diameter between ¼ inch and 3 inches. Other shaped splitters, such as a round splitter with a solid body and connections extending from the body, can be used.

The isolation valves in a preferred embodiment are high pressure ball valves which can sustain a pressure between 500 psi and 5000 psi, more preferably between 2400 psi and 5000 psi. Other types of valves can be used, including, butterfly valves, flapper, valves or block valves or combinations of these valves.

Continuing with the figures, a manifold (26) has been devised to facilitate in the distribution of the pressurized air to lower pressure breathable air with at least three and preferably eight take-out connections. More than eight take out connections can be used, including by not limited to twenty-eight take out connections. The manifold (26) can be modified to allow between two and forty-eight take-out connections for workers to connect in order to receive air to their respirators or similar devices. The manifold can be constructed of a corrosion resistant metal.

A second auxiliary air conduit segment (27) communicates between the second isolation valve (24) and the reserve manifold (26). This construction enables the breathing air system to distribute pressurized breathing air to one or more reserve manifolds from at least two directions providing grade "D" breathing air. The second auxiliary air conduit segment is a low pressure hose, such as a ⅝ inch diameter hose available from Gates Corporation. This conduit preferably is formed from neoprene, but can be a poly vinyl chloride pipe or other hard crystalline material pipe that can support low pressure breathing air.

The conduit can be a hose adapted to sustain high pressures such as part number RESP 5893 available from Total Safety US, Inc.

Figure 2:
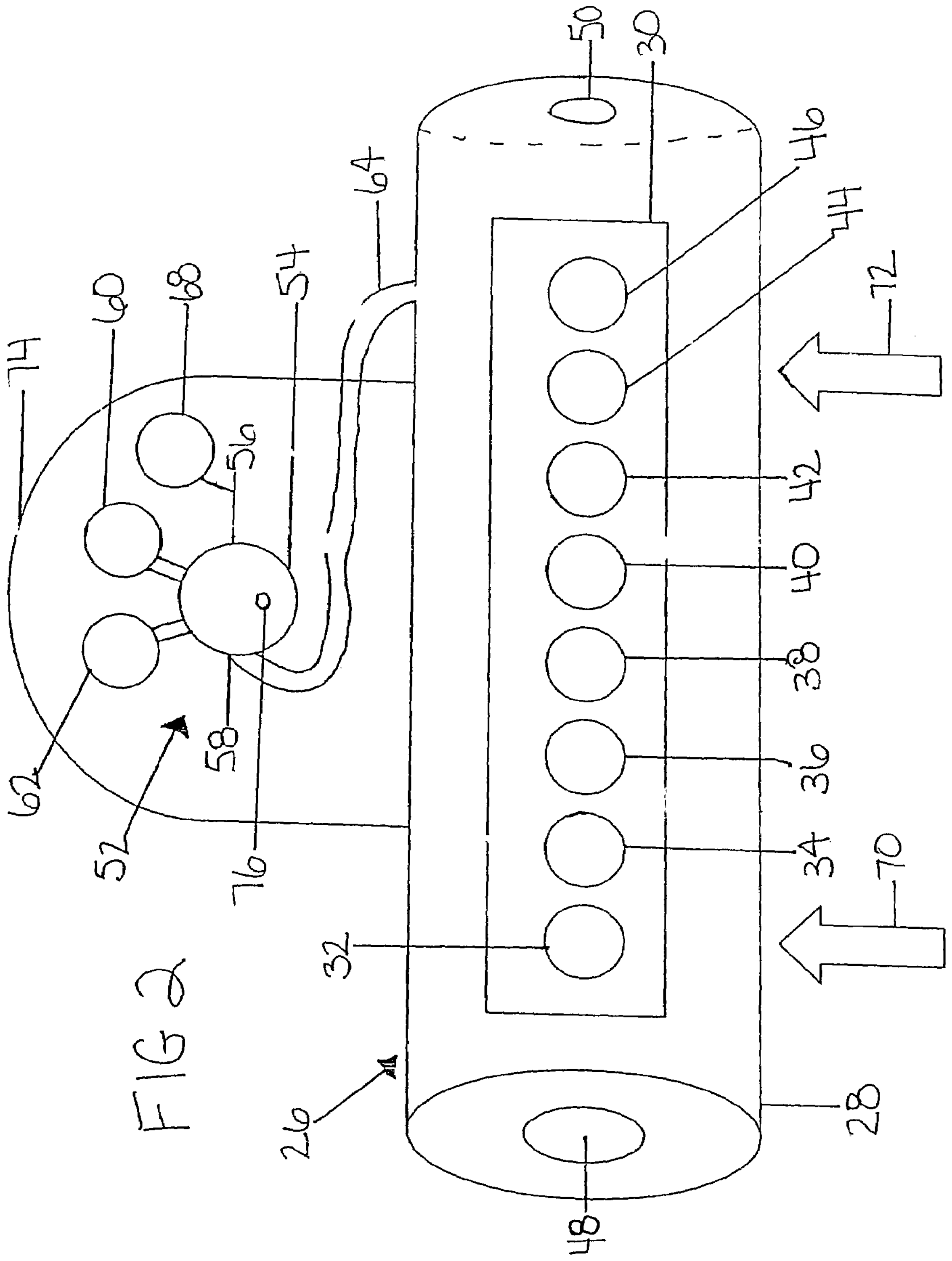
FIG. 2 depicts a detailed side view of a reserve manifold according to the system.
Figure 3:
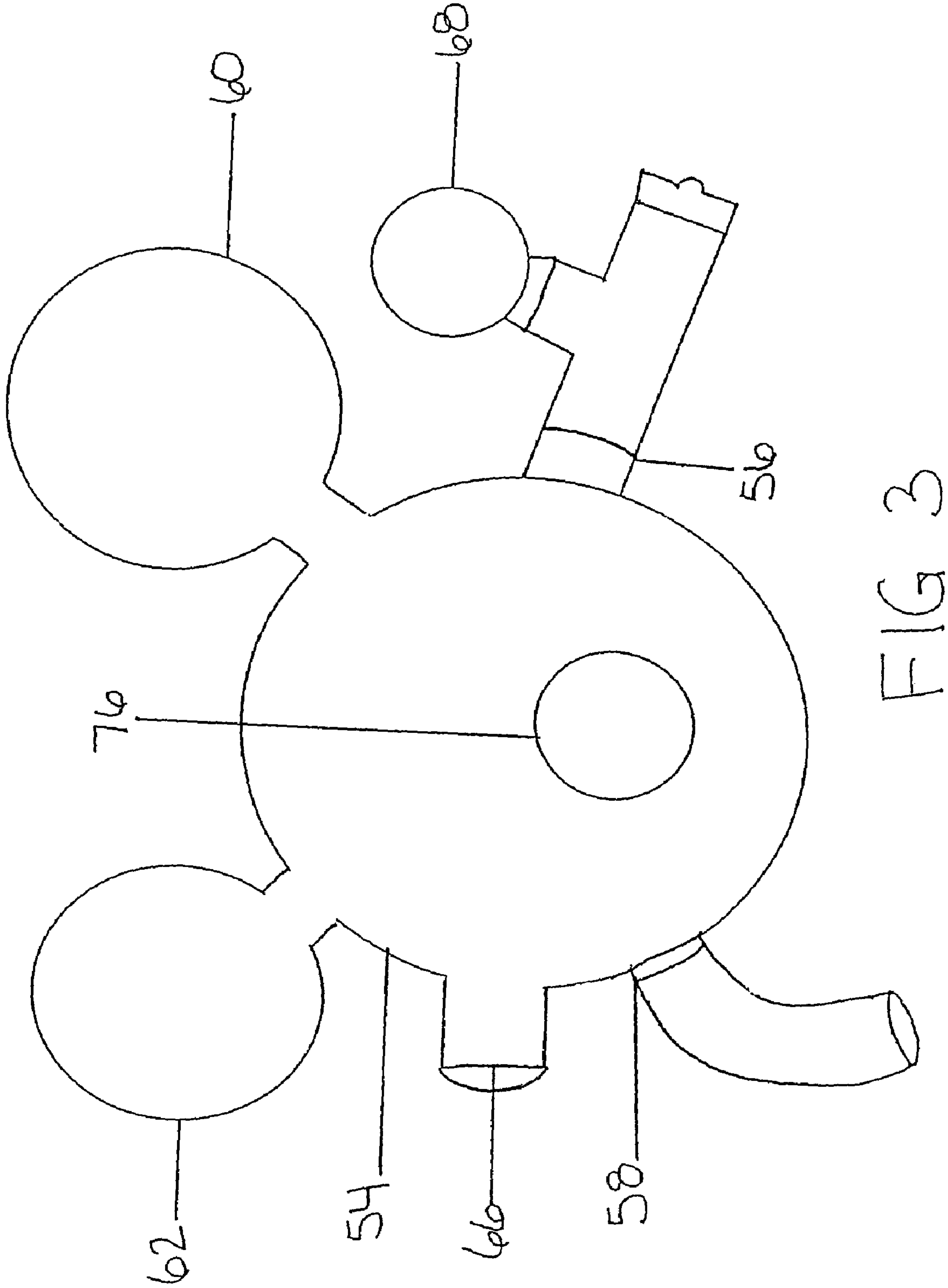
FIG. 3 depicts a detailed side view of a regulator usable in the system.

A preferred embodiment of a manifold usable here is depicted in FIG. 2. A detail of the regulator usable in the manifold is shown in FIG. 3. The figures depict an example of the manifold (26) with a manifold body (28) with a part number RESP 5587 available from Total Safety US, Inc. Preferably, this manifold body is between approximately 3 inches and 12 inches long. The reserve manifold is made of stainless steel and has one or more supports connected to the manifold body.

The manifold body has a chamber (30) within the body, which in a preferred embodiment can be a cylindrical chamber. In the most preferred embodiment, two or more take-out connections are disposed on the manifold body. Between three take-out connections and eight take-out connections are preferred. FIG. 2 shows eight take-out connections (32, 34, 36, 38, 40, 42, 44, and 46) disposed on the manifold body and connected to the chamber. The size of the chamber is dependent upon the number of desired take out connections.

A first plug (48) is located on one end of the chamber (30) and a second plug (50) is located on the other end of the chamber (30). These plugs can be screwed or threaded. In an alternative embodiment, the plugs can be welded plates. The threaded engagement for the plugs allows for multiple manifolds to connected together via the threaded engagement. The threads are not shown. An example of a plug is a one-inch hex plug made of brass and known as part number RESP 5563 available from Total Safety US, Inc.

Continuing with the figures, a regulator (52) is in fluid communication with the chamber for receiving the pressurized breathing air (15) and then reducing the pressurized breathing air to a breathable pressure. In the most preferred embodiment, the regulator is made of a regulator body (54), an inlet port (56) connected to the regulator body, and an outlet port (58) connected to the regulator body. An example of a regulator usable with the breathing system is a Victor regulator available from Masthead distributors of Clinton Drive, Houston, Tex.

An inlet pressure gauge (60) is connected to the inlet port. An outlet pressure gauge (62) is connected to outlet port to monitor and measure the pressure of the breathing air. The pressure gauges can be acquired from Mine, Safety Appliances of Pittsburgh Pa.

A regulator conduit (64) connects from the outlet port to the manifold body and communicates with the chamber. The conduits can have a inside diameter ranging from 1 inch to about 3 inches. The inside diameter of the conduits is dependent upon air flow rates desired through the breathing air conduit.

A pressure relief valve (66) is connected to the regulator body and a low pressure alarm (68) is connected to the inlet port (depicted in FIG. 3) which provides a signal, or alarm, such as a flashing light or a noise, when the air conduit pressure falls below 500 psi. One pressure relief valve per manifold is typically used.

The manifold can be supported by a mounting bracket to secure the manifold to a wall or other structure. Alternatively, as shown in FIG. 2, the manifold can have at least one support (two are shown, 70 and 72) connected to the manifold body. One embodiment of the system contemplates having between 1 manifold and 200 manifolds installed on the conduit.

A handle (74) can be connected to the manifold body to air in installation of the manifold in the system.

One or more isolation valves and one splitter can be used with each manifold used in order to maintain the loop. The isolation valves and splitters are orientated so that air moves in a continuous loop, and air can flow in either direction.

A notable benefit of the system is that the isolation valves can be locked in and tagged in, or locked out and tagged out; and, therefore, the system can be used in tandem with existing lock in and lock out systems of plants, tag in and tag out systems of plants.

The source of the breathing air can be a breathing air compressor and/or at least one cylinder of pressurized breathable air.

In one embodiment, the manifold body can be a stainless steel body with brass fittings.

FIG. 3 particularly depicts the outlet gauge as a model 0-20 Wika gauge, and the inlet gauge can be a 0-4000 model Wika gauge. The low level alarm can be a MSA 1766 low level alarm available from Total Safety US, Inc. An example of a regulator is a Gen153x regulator from Total Safety US, Inc.

The breathing air system can include a low pressure control valve (76) connected to the regulator body (54) to adjust the pressurized breathing air to a low pressure breathing air. The low pressure breathing air is between 60 psi and 125 psi.

Figure 4:
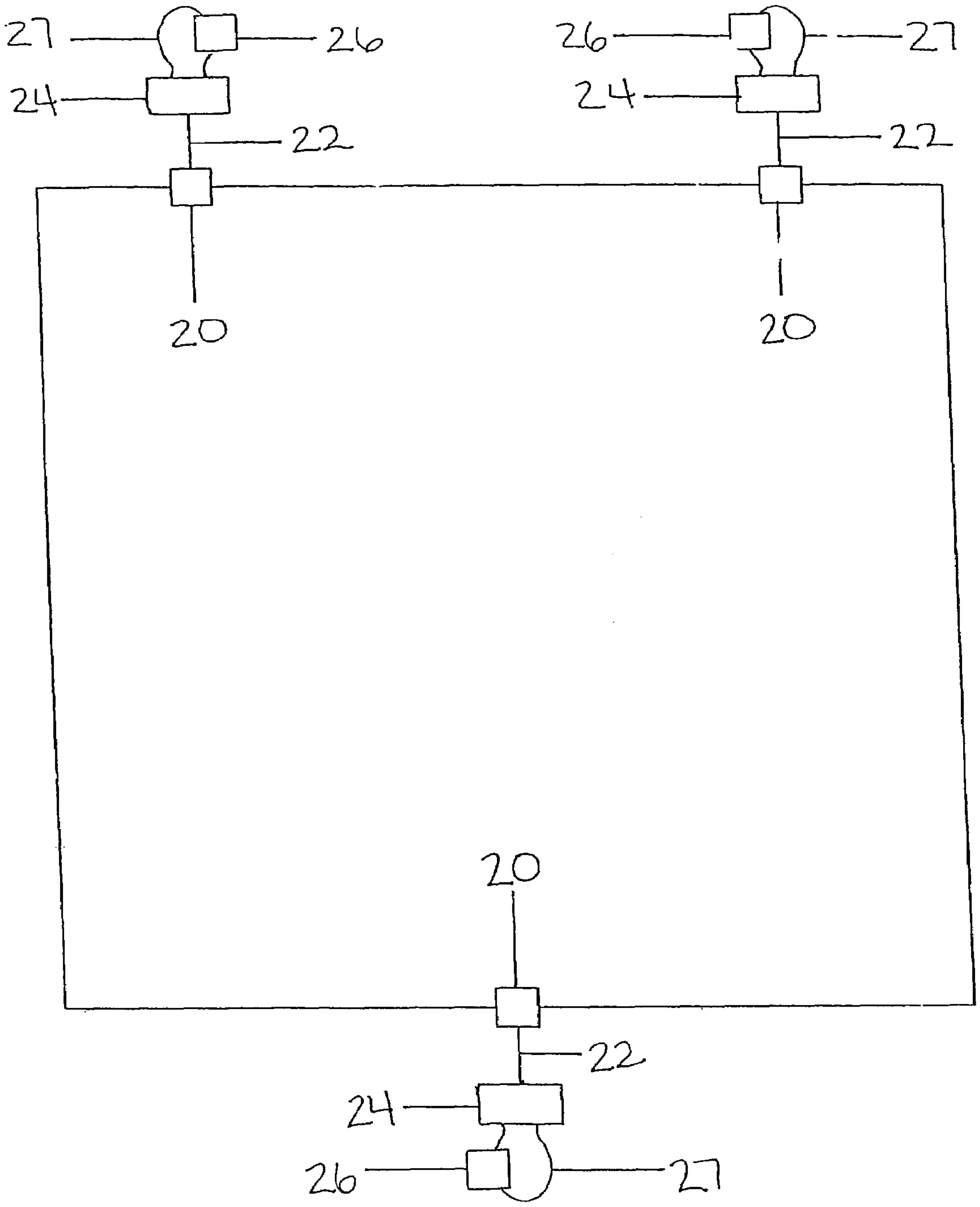
FIG. 4 depicts a schematic view of the system located within a chemical plant.

FIG. 4 depicts a diagram of the system installed in a plant with multiple reserve manifolds, multiple splitters, and multiple isolations valves shown.

Another embodiment contemplates that a sensor or transducer can be used with the regulator, and a hydraulic or a pneumatic system to sense pressure changes and then open or close the low pressure control valve. The low pressure alarm can be connected to the sensor or transducer as well as a control processing unit, such as a computer to provide control and alarm information to remote locations for continuous monitoring and adjustment of the pressure. Preferably, the low pressure control valve is manually operable.

In still another embodiment, the remote location is monitored from yet another location using a website on the Internet.

Figure 5:
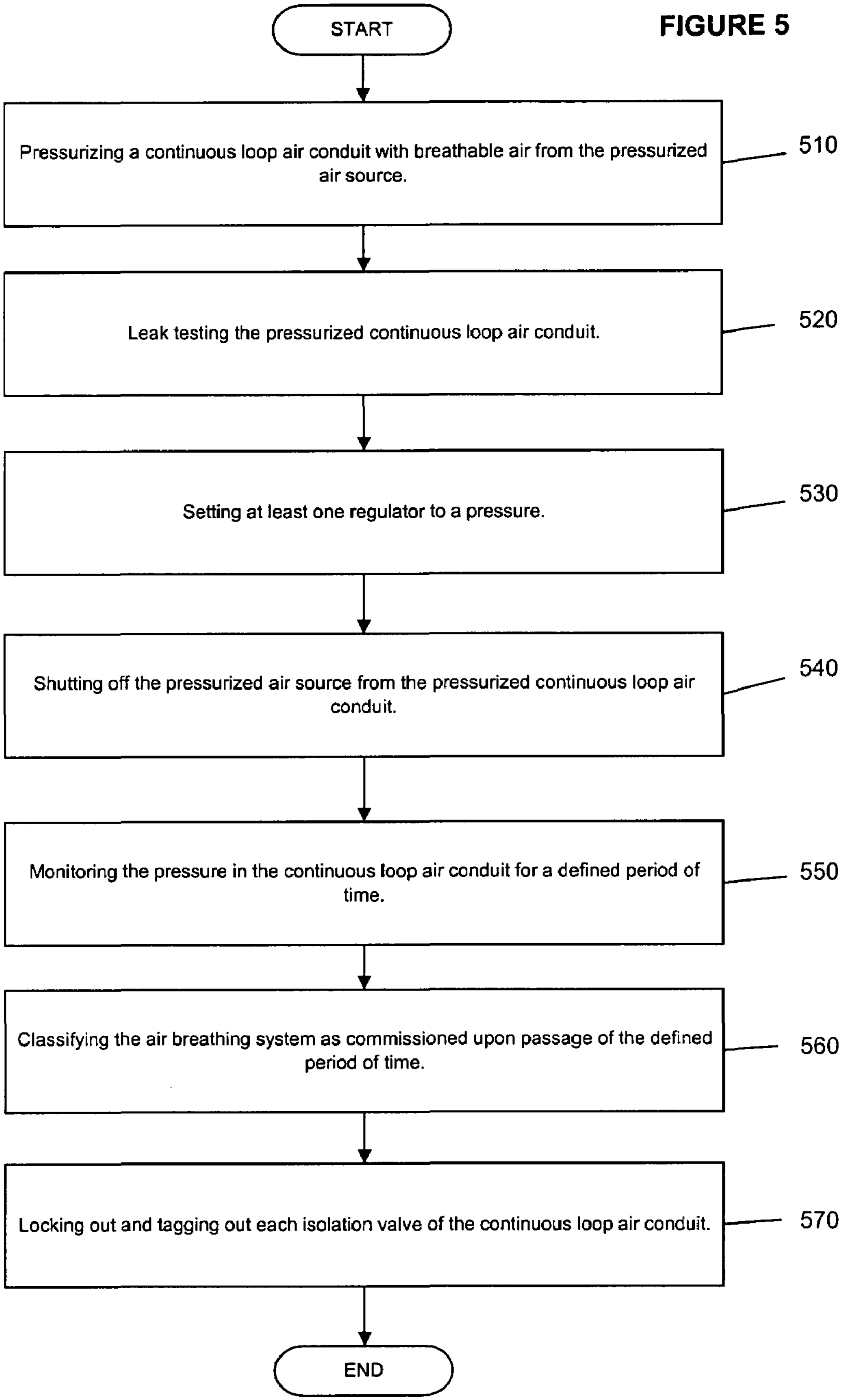
FIG. 5 is a schematic of the method for operating an air breathing system.

Referring to FIG. 5, is an example of a method for operating an air breathing system begins by pressurizing a continuous loop air conduit with breathable air from the pressurized air source (Step 510) and then leak testing the pressurized continuous loop air conduit (Step 520).

At least one regulator in the system is set to a pressure between 60 psi and 125 psi (Step 530). The pressurized air source is shut off or isolated from the pressurized continuous loop air conduit (Step 540).

The method next entails monitoring the pressure in the continuous loop air conduit for a defined period of time (Step 550) and classifying the air breathing system as commissioned upon passage of the defined period of time (Step 560). Finally, the method ends by locking out and tagging out each isolation valve of the continuous loop air conduit (Step 570).

In an alternative embodiment, the method can include the steps of locking in and tagging in each isolation valve of the continuous loop air conduit; turning on the air at the source; and continuously monitoring the system for changes in pressure.

In another embodiment, the method can include the steps of hooking up a low pressure hose to a take-out connection on the reserve manifold by at least one worker; and connecting the low pressure hose to a respirator and breathing air from the reserve manifold.

In the event of failure in the continuous loop air conduit, a low pressure alarm is sounded identifying a location of failure. Typically, the alarm is sounded when the air pressure is less than 500 psi. Any workers from the continuous loop air conduit are moved from the location of failure. The isolation valves around the location of failure are closed. Finally, the section of conduit at the location of failure is inspected while operating the continuous loop air conduit for other workers not at the location of failure. The source is breathing air from a compressor or breathing air from cylinders.

The system has been described in detail with particular reference to certain preferred embodiments thereof, but it will be understood that variations and modifications can be effected within the scope of the system, especially to those skilled in the art.

What is claimed is:

1. A breathing air system comprising:

a. a pressurized breathing air source;

b. an air conduit connected to the pressurized breathing air source;

c. a first valve disposed between the pressurized breathing air source and the air conduit;

d. a first splitter disposed between the first valve and the air conduit;

e. a second splitter connected to the air conduit;

f. a first auxiliary air conduit segment connected to the second splitter;

g. a second valve connected to the first auxiliary air conduit segment;

h. at least one manifold; and i. a second auxiliary air conduit segment communicating between the second valve and the at least one manifold, wherein the breathing air system is adapted to distribute pressurized breathing air to the at least one manifold from two directions, and wherein the manifold is adapted to provide breathing air.

2. The breathing air system of claim 1, wherein the breathing air source is at least an air quality of a Compressed Gas Association grade “D”.

3. The breathing air system of claim 1, wherein the pressurized breathing air source is pressured to between 500 psi and 5000 psi.

4. The breathing system of claim 3, wherein the pressurized breathing air source is pressured to between 2400 psi and 5000 psi.

5. The breathing air system of claim 1, wherein the air conduit is a continuous loop.

6. The breathing air system of claim 1, wherein the air conduit is pipe, tubing, hose or combinations thereof.

7. The breathing air system of claim 6, wherein the tubing is stainless steel.

8. The breathing air system of claim 1, wherein the first valve is an isolation valve.

9. The breathing air system of claim 8, wherein the isolation valve is a high pressure ball valves.

10. The breathing air system of claim 1, wherein the splitters are a T-block with an inner diameter between ¼ inch and 3 inches.

11. The breathing system of claim 1, wherein the manifold comprises a corrosion resistant metal.

12. The breathing air system of claim 1, wherein the manifold comprises:

a. a manifold body comprising a chamber;
b. at least three take-out connections disposed on the manifold body connected to the chamber;
c. a first plug on one end of the chamber and a second plug on the opposite end of the chamber; and
d. a regulator connected to the chamber for receiving the pressurized breathing air and reducing the pressurized breathing air to a breathable pressure.

13. The breathing air system of claim 12, wherein the regulator comprises:

a. a regulator body;
b. an inlet port connected to the regulator body and an outlet port connected to the regulator body;
c. an inlet pressure gauge connected to the inlet port and an outlet pressure gauge connected to outlet port;
d. a regulator conduit connected from the outlet port to the manifold body in communication with the chamber;
e. a pressure relief valve connected to the regulator body; and
f. a low pressure warning alarm connected to the inlet port which is adapted to alarm when the air conduit pressure falls below 500 psi.

14. The breathing air system of claim 13, further comprising a low pressure control valve connected to the regulator body to adjust the pressurized breathing air to a low pressure breathing air.

15. The breathing air system of claim 14, wherein the low pressure control valve is manually operable.

16. A method for operating an air breathing system comprising the steps of:

a. pressurizing a continuous loop air conduit with breathable air from a pressurized air source, wherein the continuous loop conduit comprises:
   i. a first isolation valve disposed between the pressurized air source and the continuous loop air conduit;
   ii. a first splitter disposed between the first isolation valve and the continuous loop air conduit;
   iii. a second splitter connected to the continuous loop air conduit;
   iv. a first auxiliary air conduit segment connected to the second splitter;
   v. a second isolation valve connected to the first auxiliary air conduit segment;
   vi. a reserve manifold; and
   vii. a second auxiliary air conduit segment communicating between the second isolation valve and the reserve manifold; and wherein the breathing air system is adapted to distribute high pressure breathing air to at least one reserve manifold from two direction, and wherein the reserve manifold is adapted to provide breathing air;
b. leak testing the pressurized continuous loop air conduit;
c. setting at least one regulator to a pressure between 60 psi and 125 psi;
d. shutting off the pressurized air source from the pressurized continuous loop air conduit;
e. monitoring the pressure in the continuous loop air conduit for a defined period of time between 5 minutes and 120 minutes while checking for leaks in the system;
f. classifying the air breathing system as commissioned upon passage of the defined period of time and verification that there are no leaks in the system; and
g. locking out and tagging out each isolation valve of the continuous loop air conduit.

17. The method of claim 16, further comprising the steps of:

a. locking in and tagging in each isolation valve of the continuous loop air conduit;
b. turning on the air at the source; and
c. continuously monitoring the system for changes in pressure.

18. The method of claim 16, further comprising the steps of:

a. hooking up a low pressure hose to a take-out connection on the reserve manifold by at least one worker; and
b. connecting the low pressure hose to a respirator and breathing air from the reserve manifold.

19. The method of claim 16, wherein in the event of failure in the continuous loop air conduit, the method further comprises the steps of:

a. sounding a low pressure alarm identifying a location where pressure is less than 500 psi;
b. removing any workers using the system from the continuous loop air conduit at the location where pressure is less than 500 psi
c. closing the isolation valves around the location with pressure less than 500 psi; and
d. inspecting the section of conduit at the location with pressure less than 500 psi while operating the continuous loop air conduit for other workers not at the location with pressure less than 500 psi.

* * * * *